(12) United States Patent
Holah et al.

(10) Patent No.: US 7,173,049 B2
(45) Date of Patent: Feb. 6, 2007

(54) FUNGICIDAL COMPOSITIONS

(75) Inventors: David Stanley Holah, Cambridgeshire (GB); Jane Elizabeth Dancer, Cambridge (GB); Marie-Pascale Latorse, Saint Romain De Popey (FR); Richard Mercer, Ecully (FR)

(73) Assignee: Bayer Cropscience S.A. (FR)

( * ) Notice: Subject to any disclaimer, the term of this patent is extended or adjusted under 35 U.S.C. 154(b) by 248 days.

(21) Appl. No.: 10/471,123

(22) PCT Filed: Feb. 12, 2002

(86) PCT No.: PCT/FR02/00514

§ 371 (c)(1),
(2), (4) Date: Feb. 10, 2004

(87) PCT Pub. No.: WO02/069713

PCT Pub. Date: Sep. 12, 2002

(65) Prior Publication Data

US 2004/0121986 A1    Jun. 24, 2004

(30) Foreign Application Priority Data

Mar. 8, 2001 (FR) .................................. 01 03139

(51) Int. Cl.
*A01N 43/40* (2006.01)
*A01N 57/12* (2006.01)
*A01N 59/26* (2006.01)

(52) U.S. Cl. .................. 514/357; 514/75; 514/141; 424/605; 504/100

(58) Field of Classification Search ................ 424/601, 424/604, 605; 574/344–356; 504/100; 514/75, 514/141, 357
See application file for complete search history.

(56) References Cited

U.S. PATENT DOCUMENTS 6,503,933 B1    1/2003   Moloney et al. ............ 514/357

6,828,441 B2   12/2004   Moloney et al. ............ 546/296

FOREIGN PATENT DOCUMENTS

| EP | 0398072 | 5/1990 |
| EP | 0472996 | 8/1991 |
| EP | 0775696 | 5/1995 |
| WO | WO 99/42447 | 8/1999 |
| WO | 0379788 | 10/2003 |

OTHER PUBLICATIONS

Farm Chemicals Handbook '98, Meister Publishing Co., Willoughby, Ohio, 1998, p. C 191.*
British Crop Protection Council: The Pesticide Manual, 12th Edition, CDS Tomlin (ED), Farnham, GB XP002200421, pp. 410-411, 578-581, 632-633, 659, 669, 781-782, 962-963.

* cited by examiner

*Primary Examiner*—John Pak
(74) *Attorney, Agent, or Firm*—Ostrolenk, Faber, Gerb & Soffen, LLP

(57) ABSTRACT

1) Fungicidal compositions comprising:
   a) at least one pyridylmethylbenzamide derivative of formula (I):

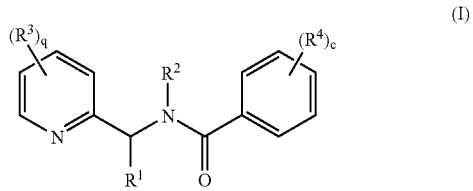

in which the various radicals are as defined in the description, and
   b) at least one compound (II) which is a phosphorous acid derivative, or phosphorous acid itself, and also alkali metal, alkaline-earth metal or metallic salts thereof.

2) Process for curatively or preventively combating the phytopathogenic fungi of crops, characterized in that an effective and non-phytotoxic amount of one of these fungicidal compositions is applied to the aerial parts of the plants.

15 Claims, No Drawings

FUNGICIDAL COMPOSITIONS

CROSS REFERENCE TO RELATED APPLICATION

The present application is a 35 U.S.C. § 371 national phase conversion of PCT/FR02/00514, filed Feb. 12, 2002, which claims priority of French Application No. 01/03139 filed Mar. 8, 2001.

The present invention relates to novel fungicidal compositions comprising at least one pyridylmethylbenzamide derivative and at least one phosphorous acid derivative, these compositions being especially intended for protecting crops. The invention also relates to a process for protecting crops against fungal diseases by applying these compositions.

Compounds of pyridylmethylbenzamide type with fungicidal action are known, especially from European patent application EP-A-1 056 723, these compounds making it possible to prevent the growth and development of phytopathogenic fungi which attack or are liable to attack crops.

Moreover, fungicidal compositions derived from phosphorous acid are already widely known in the field of treating phytopathogenic diseases of crops. Such derivatives are, for example, phosphorous acid itself and its alkali metal or alkaline-earth metal salts, and also metal phosphites such as fosetyl-Al, as described in "The Pesticide Manual", A World Compendium, 11th edition, C. D. S. Tomlin, British Crop Protection Council, page 629–630.

However, it is always desirable to improve the products which can be used by growers in order to combat fungal diseases of crops, and in particular mildews.

It is also always desirable to reduce the doses of chemical products spread into the environment to combat fungal attacks on crops, in particular by reducing the application doses of the products.

Lastly, it is always desirable to increase the number of antifungal products available to growers in order for them to find, among these products, the one which is best suited to their specific use.

One aim of the invention is thus to provide a novel fungicidal composition which is useful for the problems outlined above.

Another aim of the invention is to propose a novel fungicidal composition which is useful in the preventive and curative treatment of fungal diseases, for example of Solanacea plants, of cereals and of grapevine.

Another aim of the invention is to propose a novel fungicidal composition which is of improved efficacy against mildews, oidia, rusts and botrytis in cereals, Solanacea plants and grapevine.

Another aim of the invention is to propose a novel fungicidal composition which is of improved efficacy against mildew and/or oidium and/or botrytis in grapevine.

It has now been found that these aims may be achieved, partly or totally, by means of the fungicidal compositions according to the present invention.

One subject of the present invention is thus, firstly, fungicidal compositions comprising:

a) at least one pyridylmethylbenzamide derivative of formula (I):

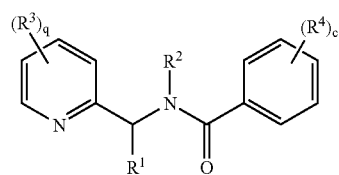

in which:

$R^1$ is chosen from a hydrogen atom, an optionally substituted alkyl radical and an optionally substituted acyl radical;

$R^2$ is chosen from a hydrogen atom and an optionally substituted alkyl radical;

$R^3$ and $R^4$, which may be identical or different, are chosen independently from a halogen atom, a hydroxyl radical, a cyano radical, a nitro radical, an —$SF_5$ radical, a trialkylsilyl radical, an optionally substituted amino radical, an acyl radical, and a group E, OE or SE, in which E is chosen from an alkyl, alkenyl, alkynyl, cycloalkyl, cycloalkenyl, aryl or heterocyclyl radical, each of them possibly being substituted;

c represents 0, 1, 2, 3 or 4;

q represents 0, 1, 2, 3 or 4;

and also possible optical and/or geometric isomers thereof, tautomers thereof and addition salts thereof with an agriculturally acceptable acid or base; and b) at least one compound (II) which is a phosphorous acid derivative, or phosphorous acid itself, and also alkali metal, alkaline-earth metal or metallic salts thereof.

In the definitions of the compounds of formula (I) outlined above, the various chemical terms and radicals used have, unless otherwise specified, the following meanings:

"alkyl" or "alkyl-" denotes a saturated, linear or branched hydrocarbon-based radical containing from 1 to 6 carbon atoms;

"alkenyl" denotes a linear or branched hydrocarbon-based radical containing from 1 to 6 carbon atoms and one unsaturation in the form of a double bond;

"alkynyl" denotes a linear or branched hydrocarbon-based radical containing from 1 to 6 carbon atoms and one unsaturation in the form of a triple bond;

"alkoxy" denotes an alkyl-oxy radical;

"acyl" denotes the formyl radical or an alkoxycarbonyl radical;

"cycloalkyl" denotes a saturated cyclic hydrocarbon-based radical containing from 3 to 8 carbon atoms;

"aryl" denotes a phenyl or naphthyl radical;

"heterocyclyl" denotes an unsaturated or totally or partially saturated cyclic radical containing from 3 to 8 atoms, chosen from carbon, nitrogen, sulphur and oxygen, for example and in a non-limiting manner, pyridyl, pyridinyl, quinolyl, furyl, thienyl, pyrrolyl, oxazolinyl;

the term "optionally substituted" means that the radicals thus qualified may be substituted with one or more radicals chosen from chlorine, bromine, fluorine, iodine, alkyl, alkoxy, hydroxyl, nitro, amino, cyano and acyl.

The compounds of formula (I) are described, for example, in patent application EP-A-1 056 723 and, among these, the compounds that will be preferred are those having one of the following characteristics, taken separately or in combination:
$R^1$ and $R^2$, which may be identical or different, are chosen independently from a hydrogen atom and an optionally substituted alkyl radical;
$R^3$ and $R^4$, which may be identical or different, are chosen independently from a halogen atom, a hydroxyl radical, a nitro radical, an optionally substituted amino radical, an acyl radical and a group E, OE or SE, in which E is chosen from an alkyl, cycloalkyl, phenyl or heterocyclyl radical, each of them possibly being substituted;
c represents 0, 1, 2 or 3;
q represents 0, 1, 2 or 3;
and also the possible optical and/or geometric isomers thereof, tautomers thereof and addition salts thereof with an agriculturally acceptable acid or base.

Among the compounds of formula (I), the compounds that will be more preferred are those having the following characteristics, taken separately or in combination:
$R^1$ and $R^2$, which may be identical or different, are chosen independently from a hydrogen atom and a methyl or ethyl radical;
$R^3$ and $R^4$, which may be identical or different, are chosen independently from a halogen atom, a nitro radical, an optionally substituted amino radical and an alkyl, cycloalkyl, phenyl or heterocyclyl radical, each of them possibly being substituted;
c represents 1 or 2;
q represents 1 or 2;
and also the possible optical and/or geometric isomers thereof, tautomers thereof and addition salts thereof with an agriculturally acceptable acid or base.

More particularly, the compounds of formula (I) have the following characteristics:
$R^1$ and $R^2$ each represent a hydrogen atom;
$R^3$ and $R^4$, which may be identical or different, are chosen independently from a halogen atom, a nitro radical, an alkyl radical and a trifluoromethyl radical;
c and q independently of each other represent 2; and also the possible tautomers thereof and addition salts thereof with an agriculturally acceptable acid or base.

By way of example, the compounds of formula (I) below are most particularly preferred in the context of the present invention:
Compound (Ia): 2,6-dichloro-N-{[3-chloro-5-(tri-fluoromethyl)-2-pyridinyl]methyl}benzamide;
Compound (Ib): N-{[3-chloro-5-(trifluoromethyl)-2-pyridinyl]methyl}-2-fluoro-6-nitrobenzamide;
Compound (Ic): N-{[3-chloro-5-(trifluoromethyl)-2-pyridinyl]methyl}-2-methyl-6-nitrobenzamide; and also the possible tautomers thereof and addition salts thereof with an agriculturally acceptable acid or base.

Among the compounds of formula (II) defined above, mention may be made, for example, of phosphorous acid itself (Compound IIa) and fosetyl-Al (Compound IIb), that is to say aluminium ethyl hydrogen phosphonate as described in "The Pesticide Manual", 11th edition, C. D. S. Tomlin, British Crop Protection Council, page 629, No. 372.

Advantageously, the compositions according to the present invention comprise compound (Ia) or compound (Ib) or compound (Ic) with compound (IIa) or compound (IIb). The preferred compositions of the present invention comprise compound (Ia) with compound (IIb) or compound (IIa).

Thus, the present invention relates to fungicidal compositions comprising at least one pyridylmethylbenzamide derivative of formula (I), as defined above, and at least one compound (II) as defined above, the compound (I)/compound (II) ratio being between 1/1 and 1/50, preferably between 1/5 and 1/25, more preferably between 1/10 and 1/20, and most particularly 1/15.

The compound (I)/compound (II) ratio is defined as being the ratio of the weight of these two compounds. This is likewise the case for any ratio of two chemical compounds mentioned subsequently in the present text, in so far as a different definition for this ratio is not expressly indicated.

It is clearly understood that the said fungicidal compositions may contain a single compound (I) or more than one such compound and/or a single compound (II) or more than one such compound, and also one or more other fungicidal, herbicidal, insecticidal and/or plant-growth-regulating compounds, depending on the use for which they are intended.

Thus, the fungicidal compositions according to the present invention may also comprise, for example, one or more other fungicidal active materials chosen from acibenzolar-S-methyl, azoxystrobin, benalaxyl, benomyl, blasticidin-S, bromuconazole, captafol, captan, carbendazim, carboxin, carpropamide, chlorothalonil, fungicidal compositions based on copper, derivatives of copper such as copper hydroxide and copper oxychloride, cyazofamide, cymoxanil, cyproconazole, cyprodinil, dichloran, diclocymet, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluquinconazole, flusilazole, flusulphamide, flutolanil, flutriafol, folpel, furalaxyl, furametpyr, guazatine, hexaconazole, hymexazol, imazalil, iprobenphos, iprodione, isoprothiolane, kasugamycin, kresoxim-methyl, mancozeb, maneb, mefenoxam, mepanipyrim, metalaxyl and their enantiomeric forms such as metalaxyl-M, metconazole, metiram-zinc, metominostrobin, oxadixyl, pefurazoate, penconazole, pencycuron, phtalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, tricyclazole, tridemorph, trifloxystrobin, triticonazole, derivatives of valinamide such as for example, iprovalicarb, vinclozolin, zineb and zoxamide.

Another subject of the invention is a process for curatively or preventively combating the phytopathogenic fungi of crops, characterized in that an effective (agronomically effective) and non-phytotoxic amount of a fungicidal composition according to the invention is applied to the soil in which the plants are growing or are liable to grow, to the leaves and/or fruit of the plants or to the plant seeds.

The compositions according to the invention are advantageous for combating especially vine mildew, for combating mildews and septoria diseases in crops, for instance cereals and market-garden crops (for example cucumber or pea), and solanacea plants, such as potatoes or tomatoes.

The compositions according to the invention may also be used for combating other phytopathogenic diseases of crops that are well known to those skilled in the art having at their disposal the compounds of formula (I) and of formula (II).

These compositions generally give an appreciable improvement in the respective and isolated actions of compound (I) and of compound (II) for a certain number of fungi that are particularly harmful to crops, especially to grapevine, more particularly to grapevine mildew, while at the same time retaining an absence of phytotoxicity with respect to these crops. This therefore results in an improvement in the spectrum of activity and a possibility of reducing the respective dose of each active material used, the latter quality being particularly important for ecological reasons that may be readily appreciated.

In the compositions according to the invention, the compound (I)/compound (II) ratio is advantageously chosen so as to produce a synergistic effect. The term "synergistic effect" especially means the effect defined by S. R. Colby in an article entitled "Calcul des responses synergiques et antagonistes des combinaisons herbicides [Calculation of the synergistic and antagonist responses of herbicidal combinations]", Weeds, (1967), 15, pages 20–22.

The said article uses the formula:

$$E = X + Y - \frac{XY}{100}$$

in which E represents the expected percentage of inhibition of the disease for the combination of the two fungicides at defined doses (for example equal to x and y, respectively), X is the percentage of inhibition observed for the disease by compound (I) at a defined dose (equal to x), Y is the percentage of inhibition observed for the disease by compound (II) at a defined dose (equal to y). When the percentage of inhibition observed for the combination is greater than E, there is a synergistic effect.

The expression "synergistic effect" also means the effect defined by applying the Tammes method "Isoboles, a graphic representation of synergism in pesticides", *Netherlands Journal of Plant Pathology*, 70 (1964), pages 73–80.

The compound (I)/compound (II) ratio ranges indicated above are in no way limiting on the scope of the invention, but rather are cited as a guide, a person skilled in the art being entirely capable of carrying out additional tests to find other values for the ratio of doses of these two compounds, for which a synergistic effect is observed.

Thus, the compositions according to the invention, comprising compound (I) and compound (II), make it possible to observe entirely noteworthy synergistic properties.

According to one variant of the compositions according to the invention, the compound (I)/compound (II) ratio is advantageously between 1/5 and 1/30 and preferably between 1/10 and 1/20.

In general, the compositions according to the invention have shown good results when the compound (I)/compound (II) ratio is equal to or in the region of 1/15.

The invention thus also comprises processes for treating plants against phytopathogenic diseases, characterized in that a composition comprising at least one compound of formula (I) is applied with at least one compound of formula (II). It is also possible to apply a composition containing the two active materials, or, either simultaneously or successively so as to have the conjugated effect, two compositions each containing one of the two active materials.

These compositions cover not only compositions which are ready to be applied to the crop to be treated by means of a suitable device, such as a spraying device, but also commercial concentrated compositions which need to be diluted before they are applied onto the crop.

The present invention provides a method for combating a large variety of phytopathogenic diseases of crops, in particular for combating Septoria leaf blotch and mildew. These diseases can be combated by direct application to the leaves.

The present invention thus provides a process for curatively or preventively combating the phytopathogenic diseases of crops, which comprises treatment of said crop (for example by application or by administration) with an effective and non-phytotoxic amount of a combination as defined above. The expression "treatment of the crop" means an application or administration of a fungicidal composition as described above onto the aerial parts of the crops or onto the soil in which they are growing and which are infested or liable to become infested with a phytopathogenic disease, such as mildew or Septoria leaf blotch, for example. The expression "treatment of the crop" also means treatment of the reproduction products of the crop, such as the seeds or the tubers, for example.

The compositions described below are used in general for application onto growing vegetation, or onto areas in which crops are grown, or for the coating of or film-forming on the seeds.

Among the means which are suitable for applying the compositions according to the invention, mention may be made of the use of powders, foliar sprays, granules, mists or foams, or alternatively means in the form of suspensions of finely divided or encapsulated compositions; for the treatment of soils or roots with liquid imbibitions, powders, granules, fumes or foams; for application onto plant seeds, the use, as agents for forming a film on or coating seeds, of powders or liquid broths.

The compositions according to the invention are, appropriately, applied to the plant and in particular to the leaves infested with the phytopathogenic fungi. Another method for applying the compounds or compositions according to the invention is to add a formulation containing the active materials, to the irrigation water. This irrigation can be an irrigation using sprinklers.

The formulations which are suitable for the applications of the compositions according to the invention comprise formulations which are suitable for use in the form, for example, of sprays, powders, granules, mists, foams, emulsions or the like.

In practice, for combating the phytopathogenic diseases of crops, one method, for example, consists in applying an effective amount of a composition according to the invention onto the plants or onto the medium in which they are growing. For such a method, the active materials are generally applied onto the same area in which the infestation needs to be controlled, at an effective dose of between about 5 g and about 5000 g of active materials in total per hectare of area treated. Under ideal conditions, depending on the nature of the phytopathogenic fungus to be treated, a lower dose may offer adequate protection. Conversely, poor climatic conditions, resistance or other factors may require higher doses of active materials.

The effective working doses of the combinations used in the invention can vary within wide proportions, in particular depending on the nature of the phytopathogenic fungi to be eliminated or the degree of infestation, for example, of the plants with these fungi.

The optimum dose usually depends on several factors, for example on the type of phytopathogenic fungus to be treated, on the type or level of development of the infested plant, on the density of vegetation, or alternatively on the method of application. More preferably, an effective dose of active materials (I) and (II) is between about 5 g/ha and about 2000 g/ha.

For their use in practice, the compositions according to the invention can be used alone and can also advantageously be used in formulations containing one or other of the active materials or alternatively both of them together, in combination or association with one or more other compatible components which are, for example, solid or liquid fillers or diluents, adjuvants, surfactants or equivalents, which are suitable for the desired use and which are acceptable for uses in agriculture. The formulations can be of any type known in the sector which are suitable for application onto all types of plantations or crops. These formulations, which can be prepared in any manner known in this sector, also form part of the invention.

The formulations can also contain ingredients of other types, such as protective colloids, adhesives, thickeners, thixotropic agents, penetrating agents, oils for spraying, stabilizers, preserving agents (in particular mouldproofing agents), sequestering agents or the like, as well as other known active ingredients which have pesticidal properties (in particular fungicidal, insecticidal, acaricidal or nematicidal properties) or which have plant-growth-regulating properties. More generally, the compounds used in the invention can be combined with any solid or liquid additives corresponding to the usual formulation techniques.

In general, the formulations according to the invention usually contain from about 0.05% to about 99% (by weight) of one or more compositions according to the invention, from about 1% to about 95% of one or more solid or liquid fillers and, optionally, from about 0.1% to about 50% of one or more other compatible compounds, such as surfactants or the like.

In the present account, the term "filler" means an organic or inorganic, natural or synthetic component with which the active components are combined to facilitate its application, for example, onto the plants, the seeds or the soil. This filler is consequently generally inert and it must be acceptable, (for example acceptable for agronomic uses, in particular for treating plants).

The filler can be solid, for example clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates. The solid fillers which are suitable for granules are as follows: natural, crushed or broken rocks, such as calcites, marble, pumice, sepiolite or dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or dyes which, when they are solid, can also act as diluents.

The fillers can also be liquids, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethylacetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type or a mixture of these surfactants. Among those surfactants which are used, for example, are polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkylphenols or arylphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the compounds described above. The presence of at least one surfactant is generally essential when the active materials and/or the inert filler are insoluble or only sparingly soluble in water and when the filler for the said composition to be applied is water.

The formulations according to the invention can also contain other additives such as adhesives or dyes. Adhesives such as carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations. It is possible to use dyes such as inorganic pigments, such as, for example: iron oxides, titanium oxides, Prussian blue; organic dyestuffs, such as those of the alizarin, azo or metal phthalocyanin type; or of trace elements such as iron, manganese, boron, copper, cobalt, molybdenum or zinc salts.

The formulations containing the compositions of the invention, which are used to combat the phytopathogenic fungi of crops, can also contain stabilizers, other fungicidal agents, insecticides, acaricides, nematicides, anti-helminths or anti-coccidoses, bactericides, attractant or repellent agents or pheromones for arthropods or vertebrates, deodorizers, flavourings or dyes.

These can be chosen for the purpose of improving the strength, the persistence, the safety, the spectrum of action on the phytopathogenic fungi of crops or to make the composition capable of accomplishing other useful functions for the areas treated.

For their agricultural use, the compositions according to the invention are consequently formulated in various solid or liquid forms.

As solid formulations, mention may be made of powders for dusting (with an active material content which can be up to 100%) and granules, in particular those obtained by extrusion, by atomization, by compacting, by impregnation of a granulated support or by granulation from a powder (the active material content in these granules being between 0.5 and 80% for the latter cases).

The fungicidal compositions according to the invention can also be used in the form of powders for dusting; formulations comprising 50 g of active materials and 950 g of talc can also be used; formulations comprising 20 g of active materials, 10 g of finely divided silica and 970 g of talc can also be used; these constituents are mixed together and ground and the mixture is applied by dusting.

As liquid formulations or formulations intended to constitute liquid compositions when applied, mention may be made of solutions, in particular water-soluble concentrates, emulsifiable concentrates, emulsions, concentrated suspensions and wettable powders (or powders for spraying).

The concentrated suspensions, which can be applied by spraying, are prepared so as to obtain a stable fluid product which does not become deposited and which gives good bioavailability of the active material(s). These suspensions usually contain from 5% to 75% of active materials, preferably from 10% to 25%, from 0.5% to 75% of surfactants, preferably from 5% to 50%, from 0% to 10% of suitable additives, such as thickeners of organic or mineral origin, antifoaming agents, corrosion inhibitors, adhesives, preserving agents, such as, for example, Proxel GXL®, antifreezes and, as support, water or an organic liquid in which the active materials are insoluble or sparingly soluble: certain organic solid materials or mineral salts may be dissolved in the support to help prevent sedimentation or as antifreezes for the water. In certain cases, and in particular for formulations intended for treating seeds, one or more dyes may be added.

For foliar applications, the choice of surfactants is paramount for obtaining good bioavailability of the active material(s); thus, a combination of a surfactant of hydrophilic nature (HLB>10) and a surfactant of lipophilic nature (HLB<5) will preferably be used. Such combinations of surfactants are disclosed, for example, in the as yet unpublished French patent application No. 00 04015.

By way of example, here are 3 possible formulations of concentrated suspension type that are suitable for various crops:

EXAMPLE CS 1 (IN g/kg)

| This example is suited rather to monocotyledon crops (cereals, rice, etc.) | |
|---|---|
| active materials | 150 |
| surfactant of hydrophilic nature (for example Rhodasurf 860P) | 300 |
| surfactant of lipophilic nature (for example Plurafac LF 700) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 255 |

EXAMPLE CS 2 (IN g/kg)

| This example is suited rather to dicotyledon crops (grapevines, fruit trees, etc.) | |
|---|---|
| active materials | 150 |
| surfactant of hydrophilic nature (for example Rhodasurf 860P) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 555 |

EXAMPLE CS 3 (IN g/kg)

| This example is more specifically suited to the treatment of seeds. | |
|---|---|
| active materials | 50 |
| surfactant of hydrophilic nature (for example Rhodasurf 860P) | 5 |
| ethoxylated tristyrylphenol phosphate | 15 |
| antifoam | 1 |
| propylene glycol | 30 |
| dye | 20 |
| Rhodopol G | 1.5 |
| Proxel GXL | 1.5 |
| water (qs 1 kg) | 876 |

The following procedure will preferably be used to prepare these formulations:

The surfactants selected (surfactant of hydrophilic nature+surfactant of lipophilic nature+ethoxylated tristyrylphenol phosphate) are mixed with the required amount of water, using a turbo mixer; after homogenization, the other constituents of the formula apart from the active materials are then mixed together.

Next, the active materials and optionally the thickener of mineral origin (Aerosil 200 and Attagel 50) are added to give a medium of viscous consistency.

The mixture obtained is then ground using a turbo mixer mill at high speed and then a ball mill until a D50 of about 1 to 3 μm and a D90 of between 3 and 8 μm are obtained.

When no thickener of mineral origin is used, the thickener of natural origin (Rhodopol G) is then added and the mixture is stirred until a suitable viscosity is obtained.

The wettable powders (or powders for spraying) are usually prepared such that they contain 20% to 95% of active materials, and they usually contain, in addition to the solid support, from 0% to 30% of a wetting agent, from 3% to 20% of a dispersant and, when necessary, from 0.1% to 10% of one or more stabilizers and/or other additives, such as penetration agents, adhesives, anticaking agents, dyes, etc.

In order to obtain the powders for spraying or wettable powders, the active materials are intimately mixed with the additional substances in suitable mixers and are ground with mills or other suitable grinders. Powders for spraying with advantageous wettability and suspension formation are obtained; they can be placed in suspension with water at any desired concentration and these suspensions can be used very advantageously, in particular for application, for example, to plant leaves or to seeds.

By way of example, there follow various wettable powder compositions (or powders for spraying):

EXAMPLE WP 1

| | |
|---|---|
| active materials | 50% |
| ethoxylated fatty alcohol (wetting agent) | 2.5% |
| ethoxylated phenylethylphenol (dispersant) | 5% |
| chalk (inert support) | 42.5% |

EXAMPLE WP 2

| active materials | 10% |
|---|---|
| synthetic C13 oxo alcohol of branched type, ethoxylated with 8 to 10 ethylene oxide (wetting agent) | 0.75% |
| neutral calcium lignosulphonate (dispersant) | 12% |
| calcium carbonate (inert filler) | qs 100% |

EXAMPLE WP 3

This wettable powder contains the same ingredients as in the above example, in the following proportions:

| active materials | 75% |
|---|---|
| wetting agent | 1.50% |
| dispersant | 8% |
| calcium carbonate (inert filler) | qs 100% |

EXAMPLE WP 4

| active materials | 90% |
|---|---|
| ethoxylated fatty alcohol (wetting agent) | 4% |
| ethoxylated phenylethylphenol (dispersant) | 6% |

EXAMPLE WP 5

| active materials | 50% |
|---|---|
| mixture of anionic and nonionic surfactants (wetting agent) | 2.5% |
| sodium lignosulphonate (dispersant) | 5% |
| kaolinic clay (inert support) | 42.5% |

The aqueous dispersions and emulsions, for example the compositions obtained by diluting a wettable powder according to the invention with water, are included within the general scope of the present invention. The emulsions can be of the water-in-oil or oil-in-water type and they can have a thick consistency, such as that of a "mayonnaise".

The fungicidal compositions according to the invention can be formulated in the form of water-dispersible granules, which are also included within the scope of the invention. These dispersible granules, with an apparent density generally of between about 0.3 and 0.6, have a particle size generally of between about 150 and 2000 and preferably between 300 and 1500 microns.

The active material content of these granules is generally between about 1% and 90% and preferably between 25% and 90%. The rest of the granule is essentially composed of a solid filler and optionally of surfactant adjuvants which give the granule water-dispersibility properties. These granules can be essentially of two different types depending on whether the filler selected is soluble or insoluble in water. When the filler is water-soluble, it can be inorganic, or, preferably, organic. Excellent results have been obtained with urea. In the case of an insoluble filler, it is preferably inorganic, such as for example kaolin or bentonite. It is then advantageously accompanied by surfactants (in a proportion of from 2 to 20% by weight of the granule) more than half of which consists, for example, of at least one dispersant, which is essentially anionic, such as an alkali metal or alkaline-earth metal polynaphthalene sulphonate or an alkali metal or alkaline-earth metal lignosulphonate, the remainder consisting of nonionic or anionic wetting agents such as an alkali metal or alkaline-earth metal alkylnaphthalene sulphonate. Moreover, although this is not essential, other adjuvants can be added, such as antifoaming agents.

The granule according to the invention can be prepared by mixing together the required ingredients, followed by granulation according to several techniques which are known per se (granulator, fluid bed, sprayer, extrusion, etc.). The process generally ends with a crushing operation, followed by an operation of screening to the particle size chosen within the limits mentioned above. Granules obtained as above and then impregnated with a composition containing the active materials can also be used.

Preferably, it is obtained by extrusion, by performing the process as indicated in the examples below.

EXAMPLE DG1

Dispersible Granules

90% by weight of active materials and 10% of urea pellets are mixed together in a mixer. The mixture is then ground in a toothed roll crusher. A powder is obtained, which is moistened with about 8% by weight of water. The wet powder is extruded in a perforated-roller extruder. A granulate is obtained, which is dried and then crushed and screened, so as to retain, respectively, only the granules between 150 and 2000 microns in size.

EXAMPLE DG2

Dispersible Granules

The constituents below are mixed together in a mixer:

| active materials | 75% |
|---|---|
| wetting agent (sodium alkylnaphthalene sulphonate) | 2% |
| dispersant (polysodium naphthalene sulphonate) | 8% |
| water-insoluble inert filler (kaolin) | 15% |

This mixture is granulated in a fluid bed, in the presence of water, and then dried, crushed and screened so as to obtain granules between 0.15 and 0.80 mm in size.

These granules can be used alone, or as a solution or dispersion in water so as to obtain the desired dose. They can also be used to prepare compositions with other active materials, in particular fungicides, the latter being in the form of wettable powders, granules or aqueous suspensions.

The fungicidal compositions according to the invention usually contain from 0.5 to 95% of the combination of compound (I) and compound (II). This may be the concentrated composition, that is to say the commercial product combining compound (I) and compound (II). It may also be the dilute composition ready to be applied to the crops to be treated. In the latter case, the dilution with water may be carried out either using a commercial concentrated composition containing compound (I) and compound (II) (this mixture is referred to as "ready mix"), or using the mixture prepared at the time of use (known as the "tank mix") of two commercial concentrated compositions each containing compound (I) and compound (II).

Lastly, the subject of the invention is a process for curatively or preventively combating the phytopathogenic fungi of crops, characterized in that an effective and nonphytotoxic amount of a fungicidal composition according to the invention is applied to the vegetation to be treated.

The phytopathogenic fungi of the crops which may be combated by this process are, in particular, those:

of the group of oomycetes:
  of the genus *Phytophthora* such as *Phytophthora infestans* (mildew of Solanaceae, in particular potato or tomato mildew),
  of the family of Peronosporaceae, in particular *Plasmopara viticola* (downy mildew of grapevine), *Plasmopara halstedii* (sunflower mildew), *Pseudoperonospora* sp (in particular cucurbit mildew and downy mildew of hop), *Bremia lactucae* (mildew of lettuce), *Peronospora tabacinae* (downy mildew of tobacco) and *Peronospora parasitica* (downy mildew of cabbage), *Peronospora viciae* (downy mildew of pea) and *Peronospora destructor* (downy mildew of onion);

of the group of adelomycetes:
  of the genus *Alternaria*, for example *Alternaria solani* (early blight of Solanaceae and in particular of tomato and potatoes),
  of the genus *Guignardia*, in particular *Guignardia bidwelli* (black rot of grapevine),
  of the genus *Oidium*, for example powdery mildew of grapevine (*Uncinula necator*); powdery mildew of leguminous crops, for example *Erysiphe polygoni* (powdery mildew of Cruciferae); *Leveillula taurica, Erysiphe cichoracearum, Sphaerotheca fuligena*; (powdery mildew of cucurbits, of composites and of tomato); *Erysiphe communes* (powdery mildew of beetroot and cabbage); *Erysiphe pisi* (powdery mildew of pea and alfalfa); *Erysiphe polyphaga* (powdery mildew of bean and cucumber mildew); *Erysiphe umbelliferarum* (powdery mildew of umbellifera, in particular of carrot); *Sphaerotheca humuli* (hop mildew);

of the group of soil fungi:.
  of the genus *Pythium* sp.,
  of the genus *Aphanomyces* sp., in particular *Aphanomyces euteiches* (white root rot in pea), *Aphanomyces cochlioides* (black rot of beet).

The expression "are applied to the vegetation to be treated" is understood to mean, for the purposes of the present text, that the fungicidal compositions which form the subject of the invention may be applied by means of various treatment processes such as:

spraying a liquid comprising one of the said compositions onto the aerial parts of the said vegetation, dusting, incorporation of granules or powders into the soil, watering around the said vegetation and, in the case of trees, injection or painting, coating of or formation of a film on seeds of the said vegetation using a broth comprising one of the said compositions.

The spraying of a liquid onto the aerial parts of the crops to be treated is the preferred treatment process.

The examples which follow are given purely for the purposes of illustrating the invention and do not limit it in any way.

Although the invention has been described in terms of numerous preferred variants, a person skilled in the art will appreciate that many modifications, substitutions, omissions and changes can be made without departing from the spirit of this invention. Thus, it is clearly understood that the scope of the present invention is limited only by the scope of the following claims, as well as by their equivalents.

EXAMPLE

Test of a composition against downy mildew of grapevine (*Plasmopara viticola*; preventive action):

Protocol

Grapevine plants (Chardonnay variety) are grown on sandy soil in plastic pots, with one plant per pot. The two-month-old plants (6 to 7 leaves developed) are sprayed with compound (I) and compound (II), either alone or as a mixture.

The fungicidal active materials, either alone or as a mixture, are applied at a rate of 500 liters/ha.

The compound (I)/compound (II) ratios studied are 1/10, 1/15 and 1/20.

Three days after the treatment, each plant is inoculated by spraying with an aqueous suspension of *Plasmopara viticola* spores obtained from contaminated leaves. The spore concentration is about 100 000 units per ml.

After contamination, the plants are incubated for two days at 18° C. under a saturated atmosphere, and then for 5 days at about 20° C. with a relative humidity of 90–100%.

Seven days after the contamination, the symptoms are evaluated in terms of extent of surface area on the underside of the leaves that are infected, relative to the untreated but contaminated plants.

The efficacy of the treatment is calculated using the Abbott formula below:

$$\text{Efficacy} = \frac{(\text{untreated}) - \text{treated}}{\text{untreated}} \times 100$$

Calculation and Analysis

The concentrations of the fungicides alone or as a mixture giving 50%, 70% or 90% efficacy for each component, in the appropriate test, are determined on the basis of the model of the dose/response sigmoid curve and their corresponding confidence intervals. The results are analysed using the Tammes or Colby model.

Test on Compound (Ia) and Compound (IIa):

|  | Concentration (mg/l) | % Efficacy | Synergism (Colby) |
|---|---|---|---|
| Compound (Ia) | 10 | 77 | — |
|  | 100 | 100 | — |
| Compound (IIa) | 70 | 0 | — |
|  | 105 | 0 | — |
|  | 140 | 0 | — |
|  | 700 | 4 | — |
|  | 1050 | 50 | — |
|  | 1400 | 52 | — |
| Compound (Ia) + compound (IIa) 1/10 | 10 + 70 | 76 | −1 |
|  | 100 + 700 | 100 | 0 |

-continued

| | Concentration (mg/l) | % Efficacy | Synergism (Colby) |
|---|---|---|---|
| Compound (Ia) + compound (IIa) 1/15 | 10 + 105 | 98 | 21 |
| | 100 + 1050 | 100 | 0 |
| Compound (Ia) + compound (IIa) 1/20 | 10 + 140 | 92 | 15 |
| | 100 + 1400 | 100 | 0 |

Untreated control: 52% of sporulated surface area

The compositions according to the invention comprising compound (Ia) and compound (IIa) in a 1/15 ratio, at respective concentrations of 10 and 105 g/l make it possible to considerably reduce the doses of active materials to obtain an excellent efficacy. These same compositions at these same doses show strong synergism.

Test on Compound (Ia) and Compound (IIb):

| | Concentration (mg/l) | % Efficacy | Synergism (Colby) |
|---|---|---|---|
| Compound (Ia) | 10 | 77 | — |
| | 100 | 100 | — |
| Compound (IIb) | 100 | 0 | — |
| | 150 | 0 | — |
| | 200 | 0 | — |
| | 1000 | 46 | — |
| | 1500 | 60 | — |
| | 2000 | 81 | — |
| Compound (Ia) + compound (IIb) 1/10 | 10 + 100 | 92 | 15 |
| | 100 + 1000 | 100 | 0 |
| Compound (Ia) + compound (IIb) 1/15 | 10 + 150 | 100 | 23 |
| | 100 + 1500 | 100 | 0 |
| Compound (Ia) + compound (IIb) 1/20 | 10 + 200 | 98 | 12 |
| | 100 + 2000 | 100 | 0 |

Untreated control: 52% of sporulated surface area

The compositions according to the invention comprising compound (Ia) and compound (IIb) in a 1/15 ratio, at respective concentrations of 10 and 150 g/l make it possible to considerably reduce the doses of active materials to obtain an excellent efficacy. These same compositions at these same doses show strong synergism.

The invention claimed is:

1. A synergistic fungicidal composition comprising:
    a) a compound (I) is 2,6-dichloro-N-{[3-chloro-5-(trifluoromethyl)-2-pyridinyl]methyl}benzamide; and
    b) a compound (II) which is phosphorous acid or fosetyl-Al;
wherein the compound (I)/phosphorous acid ratio is 1/15 to 1/50 and the compound (I)/fosetyl-Al ratio is 1/1 to 1/50.

2. The fungicidal compositions according to claim 1, wherein the compound (I)/phosphorous acid ratio is 1/15 to 1/25 and the compound (I)/fosetyl-Al ratio is 1/5 to 1/25.

3. The fungicidal compositions according to claim 1, wherein the compound (I)/phosphorous acid ratio is 1/15 to 1/20 and the compound (I)/fosetyl-Al ratio is 1/10 to 1/20.

4. The fungicidal compositions according to claim 1, wherein the compound (I)/phosphorous acid ratio is 1/15 and the compound (I)/fosetyl-Al ratio is equal to or in the region of 1/15.

5. The fungicidal compositions according to claim 1, further comprising an agriculturally suitable inert support and optionally an agriculturally suitable surfactant.

6. The fungicidal compositions according to claim 1, wherein the composition comprises from 0.5 to 99% of the combination of compound (I) and compound (II).

7. A process for combating the phytopathogenic fungi of crops, characterized in that an agronomically effective and non-phytotoxic amount of a fungicidal composition according to claim 1 is applied to the soil in which the plants are growing or are liable to grow, to the leaves and/or fruit of the plants or to the plant seeds.

8. The process according to claim 7, characterized in that the fungicidal composition is applied by spraying a liquid that contains the fungicidal composition to the aerial parts of the crops to be treated.

9. The process according to claim 8, characterized in that the amount of fungicidal composition corresponds to a dose of compound (I) and of compound (II) of between about 5 and about 2000 g/ha.

10. The process according to claim 7, characterized in that the amount of fungicidal composition corresponds to a dose of compound (I) and of compound (II) of between about 5 and about 2000 g/ha.

11. A process according to claim 10, characterized in that the treated crop is grapevine.

12. The process according to claim 7, characterized in that the treated crop is grapevine.

13. The process according to claim 12, characterized in that the phytopathogenic fungus treated is downy mildew of grapevine.

14. A product comprising a compound (I) and a compound (II), as a combined preparation for simultaneous, separate or sequential use in combating the phytopathogenic fungi of crops in a site, wherein;
    a) the compound (I) is 2,6-dichloro-N-{[3-chloro-5-(trifluoromethyl)-2-pyridinyl]methyl}benzamide;
    b) the compound (II) is phosphorous acid or fosetyl-Al; and
    c) the compound (I)/phosphorous acid ratio is 1/15 to 1/50 and the compound (I)/fosetyl-Al ratio is 1/1 to 1/50.

15. The product according to claim 14, wherein the compound (I)/phosphorous acid ratio is 1/15 to 1/25 and the compound (I)/fosetyl-Al ratio is 1/5 to 1/25.

* * * * *